US008911456B2

(12) United States Patent
McCutcheon et al.

(10) Patent No.: US 8,911,456 B2
(45) Date of Patent: Dec. 16, 2014

(54) METHODS AND DEVICES FOR PREVENTING TISSUE BRIDGING WHILE SUTURING

(71) Applicant: Ceterix Orthopaedics, Inc., Menlo Park, CA (US)

(72) Inventors: John G. McCutcheon, Menlo Park, CA (US); David H. Heagy, Hermosa Beach, CA (US); Alan B. Miller, Jamison, PA (US); Christopher P. Bender, Oakland, CA (US); Michael J. Hendricksen, Redwood City, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 54 days.

(21) Appl. No.: 13/759,000

(22) Filed: Feb. 4, 2013

(65) Prior Publication Data

US 2014/0222029 A1    Aug. 7, 2014

(51) Int. Cl.
*A61B 17/04* (2006.01)

(52) U.S. Cl.
CPC .................................. *A61B 17/0493* (2013.01)
USPC ......................................................... 606/144

(58) Field of Classification Search
None
See application file for complete search history.

(56) References Cited

U.S. PATENT DOCUMENTS

| | | | |
|---|---|---|---|
| 1,037,864 A | 9/1912 | Carlson et al. |
| 2,738,790 A | 3/1956 | Todt, Sr. et al. |
| 2,748,773 A | 6/1956 | Vacheresse, Jr. |
| 3,470,875 A | 10/1969 | Johnson |
| 3,580,256 A | 5/1971 | Wilkinson et al. |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |

(Continued)

FOREIGN PATENT DOCUMENTS

| | | |
|---|---|---|
| CN | 101297765 A | 11/2008 |
| EP | 0647431 A2 | 4/1995 |

(Continued)

OTHER PUBLICATIONS

Hendricksen et al.; U.S. Appl. No. 14/265,848 entitled "Suture passer with radiused upper jaw," filed Apr. 30, 2014.

(Continued)

*Primary Examiner* — Tuan V Nguyen
(74) *Attorney, Agent, or Firm* — Shay Glenn LLP

(57) ABSTRACT

Suture passers and methods of suturing tissue to prevent tissue bridging, without requiring a cannula. Tissue bridging involves the capture of non-target tissue within a loop of suture formed around and/or through a target tissue. The devices and methods described herein may include the use of a threading aperture at or near the distal end of the suture passer to guide the device in passing a suture through the tissue along the same pathway that another leg or legs of the loop took to access the target tissue, thereby preventing the inadvertent capture of non-target tissue leading to tissue bridging. In particular, described herein are suture passers and methods of arthroscopically suturing the meniscus of the knee while preventing tissue bridging.

14 Claims, 14 Drawing Sheets

(56) References Cited

U.S. PATENT DOCUMENTS

| | | |
|---|---|---|
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,112,344 A | 5/1992 | Petros |
| 5,129,912 A | 7/1992 | Noda et al. |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,532 A | 4/1995 | Loew et al. |
| 5,431,666 A | 7/1995 | Sauer et al. |
| 5,437,681 A | 8/1995 | Meade et al. |
| 5,454,823 A | 10/1995 | Richardson et al. |
| 5,454,834 A | 10/1995 | Boebel et al. |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,800,445 A | 9/1998 | Ratcliff et al. |
| 5,814,054 A | 9/1998 | Kortenbach et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,159,224 A | 12/2000 | Yoon |
| 6,190,396 B1 | 2/2001 | Whitin et al. |
| 6,221,085 B1 | 4/2001 | Djurovic |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,491,212 B2 | 2/2009 | Sikora et al. |

(56) References Cited

U.S. PATENT DOCUMENTS

| | | |
|---|---|---|
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,394,112 B2 | 3/2013 | Nason |
| 8,449,533 B2 | 5/2013 | Saliman et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0282098 A1 | 12/2006 | Shelton et al. |
| 2007/0032799 A1 | 2/2007 | Pantages et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0294256 A1 | 11/2008 | Hagan et al. |
| 2009/0012538 A1 | 1/2009 | Saliman et al. |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105751 A1 | 4/2009 | Zentgraf |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2010/0331863 A2 | 12/2010 | Saliman |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0112555 A1 | 5/2011 | Overes et al. |
| 2011/0112556 A1 | 5/2011 | Saliman |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0218557 A1 | 9/2011 | Saliman |
| 2011/0251626 A1 | 10/2011 | Wyman et al. |
| 2011/0270280 A1 | 11/2011 | Saliman |
| 2012/0179254 A1 | 7/2012 | Saliman |
| 2012/0239062 A1 | 9/2012 | Saliman et al. |
| 2012/0283750 A1 | 11/2012 | Saliman et al. |
| 2012/0283753 A1 | 11/2012 | Saliman et al. |
| 2012/0283754 A1 | 11/2012 | Murillo et al. |
| 2012/0303046 A1 | 11/2012 | Stone et al. |
| 2013/0072948 A1 | 3/2013 | States, III et al. |
| 2013/0238040 A1 | 9/2013 | Saliman et al. |
| 2013/0253647 A1 | 9/2013 | Saliman et al. |

FOREIGN PATENT DOCUMENTS

| | | |
|---|---|---|
| JP | 3032847 U | 3/1991 |
| JP | 2009138029 A | 6/2009 |
| JP | 2009538190 | 11/2009 |
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2010/141695 A1 | 12/2010 |

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

(56) References Cited

OTHER PUBLICATIONS

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Strobel; Manual of Arthroscopic Surgery (1st Edition); Springer Verlag, Hiedelberg © 2002; pp. 127-129; Dec. 15, 2001.

USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.

USS SportsMedicine ArthoSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

Hirotsuka et al.; U.S. Appl. No. 13/758,994 entitled "Pre-Tied Surgical Knots for Use With Suture Passers," filed Feb. 4, 2013.

Saliman, J.; U.S. Appl. No. 13/759,006 entitled "Suture Passers," filed Feb. 4, 2013.

Hendricksen et al.; U.S. Appl. No. 13/844,252 entitled "Suture passers and methods of passing suture," filed Mar. 15, 2013.

Duerig, T. et al., "An overview of nitinol medical applications" Materials Science and Engineering A273-275, May 1999.

Murillo et al.; U.S. Appl. No. 13/893,154 entitled "Suture passer devices and methods," filed May 13, 2013.

Nord et al.; Posterior lateral meniscal root tears and meniscal repair; Orthopedics Today; 5 pgs; Nov. 2010; Aug. 21, 2014; retrieved from the internet (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Saliman; U.S. Appl. No. 14/292,695 entitled "Suture methods for forming locking loops stitches," filed May 30, 2014.

METHODS AND DEVICES FOR PREVENTING TISSUE BRIDGING WHILE SUTURING

CROSS REFERENCE TO RELATED APPLICATIONS

This application does not claim priority to any other patent application.

The suture passer devices and methods described herein may be used, in particular, with, or as part of any of the suture passer devices and systems described in the following patent applications, each of which is herein incorporated by reference in its entirety. Specifically: U.S. patent application Ser. No. 11/773,388, filed on Jul. 3, 2007, titled "METHODS AND DEVICES FOR CONTINUOUS SUTURE PASSING," now Publication No. US-2009-0012538-A1; U.S. patent application Ser. No. 12/972,222, filed on Dec. 17, 2010, titled "METHODS AND DEVICES FOR CONTINUOUS SUTURE PASSING," now Publication No. US-2011-0087246-A1; U.S. patent application Ser. No. 13/462,760, filed on May 2, 2012, titled "METHODS OF MENISCUS REPAIR," now Publication No. US-2012-0239062-A1; U.S. patent application Ser. No. 13/006,966, filed on Jan. 14, 2011, titled "METHODS FOR CONTINUOUS SUTURE PASSING," now Publication No. US-2011-0130773-A1; U.S. patent application Ser. No. 13/090,089, filed on Apr. 19, 2011, titled "METHODS OF MENISCUS REPAIR," now Publication No. US-2011-0218557-A1; U.S. patent application Ser. No. 12/291,159, filed on Nov. 5, 2008, titled "SUTURE PASSING INSTRUMENT AND METHOD," now Publication No. US-2010-0331863-A2; U.S. patent application Ser. No. 12/972,168, filed on Dec. 17, 2010, titled "SUTURE PASSING INSTRUMENT AND METHOD," now Publication No. US-2011-0152892-A1; U.S. patent application Ser. No. 13/062,664, filed on Apr. 19, 2011, titled "KNOTLESS SUTURE ANCHORS," now Publication No. US-2011-0190815-A1; U.S. patent application Ser. No. 12/620,029, filed on Nov. 17, 2009, titled "METHODS OF SUTURING AND REPAIRING TISSUE USING A CONTINUOUS SUTURE PASSER DEVICE," now Publication No. US-2010-0130990-A1; U.S. patent application Ser. No. 12/942,803, filed on Nov. 9, 2010, titled "DEVICES, SYSTEMS AND METHODS FOR MENISCUS REPAIR," now Publication No. US-2011-0112556-A1; U.S. patent application Ser. No. 13/462,728, filed on May 2, 2012, titled "DEVICES, SYSTEMS AND METHODS FOR MENISCUS REPAIR," now Publication No. US-2012-0265221-A1; U.S. patent application Ser. No. 13/114,983, filed on May 24, 2011, titled "SUTURING AND REPAIRING TISSUE USING IN VIVO SUTURE LOADING," now Publication No. US-2011-0270280-A1; U.S. patent application Ser. No. 13/347,184, filed on Jan. 10, 2012, titled "IMPLANT AND METHOD FOR REPAIR OF THE ANTERIOR CRUCIATE LIGAMENT," now Publication No. US-2012-0179254-A1; U.S. patent application Ser. No. 13/247,892, filed on Sep. 28, 2011, titled "MENISCUS REPAIR," now Publication No. US-2012-0283750-A1; U.S. patent application Ser. No. 13/323,391, filed on Dec. 12, 2011, titled "SUTURE PASSER DEVICES AND METHODS," now Publication No. US-2012-0283753-A1; and U.S. patent application Ser. No. 13/462,773, filed on May 2, 2012, titled "SUTURE PASSER DEVICES AND METHODS," now Publication No. US-2012-0283754-A1, each of which is incorporated by reference in its entirety.

Many of the techniques, methods and devices described herein were developed for use with one or more of these suture passer devices, and thus may be particularly well adapted for use with these systems. However, the methods and systems (and particularly the use of a suture following structure such as the threading apertures described herein) may also be used with other suture passers.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to suture passers and methods of using them to form knots with sutures while avoiding the unwanted capture of tissue, which may be referred to as "tissue bridging" or "suture bridging." These methods and systems are of particular use with arthroscopic methods, and particularly arthroscopic repair of the knee (e.g., meniscus), the shoulder (e.g., rotator cuff repair, shoulder labrum repair) and the hip (e.g., hip labrum repair).

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

A complete loop of suture may be tightened around tissue so that different regions of tissue may be placed against each other (approximating both sides of a torn or injured tissue) to promote appropriate healing. Passing a loop of suture completely around a torn or damaged tissue, and thereby applying tensioning force across an entire length of the damage tissue, has been shown experimentally to result in superior healing, preventing re-tearing of the tissue.

When using a suture passer to arthroscopically form a loop of suture around damaged tissue, multiple passes of a suture through the tissue are performed by removing the suture passer from the tissue after one or more passes of the suture, requiring the suture passer to be re-inserted to make additional passes of suture and complete the loop. Unfortunately, when a suture passer is withdrawn and then re-inserted into the tissue, additional (non-target) tissue maybe inadvertently entrapped between the ends of the suture, preventing the suture loop from being closed tightly. This is referred to as "tissue bridging" or "suture bridging".

Although tissue bridging is particularly problematic in arthroscopic surgery, it can occur in other (e.g., open) procedures as well.

This problem is well known in repairing a torn meniscus of the knee. For example, Strobel describes ("Manual of Arthroscopic Surgery" by Michael Strobel, Springer (Heidelberg: 2002), pages 127-129) a method of repairing a complete longitudinal tear of the lateral meniscus using a knot pusher to secure a loop of suture around the tear. Strobel suggests that, if a tissue bridge is formed between the sutures when securing them, the bridging tissue should be transected, or if it cannot be cleared, the suture must be completely removed and a new suture placed. This is undesirable, as it adds additional time and complication to the procedure.

In addition to cutting the bridging tissue or removing (and replacing) the suture, it has been suggested in the prior art that a large-bore cannula may be used to prevent tissue bridging. Unfortunately, such cannula may be difficult to work with, as they may slip and change position, and may limit the maneuverability of the surgical devices during a procedure.

Thus, it would be desirable to provide a device such as a suture passer that may be used to pass a loop of suture without inadvertently capturing non-target tissue, and forming a tissue bridge, even when the suture passer is removed from the patient and reinserted between suture passes. Further, it would be desirable to provide a method of suturing a tissue that prevents and avoids tissue bridging. Described herein are methods and devices, including suture passers, that may address the problems identified above.

SUMMARY OF THE DISCLOSURE

When passing multiple lengths of suture through tissue to loop around a target tissue, if the path through the non-target tissue taken by each length of suture to get to the target tissue is not the same for each length of suture passed, the non-target tissue can be entrapped between lengths of suture. This entrapment prevents the central bite of the suture from traveling to the surface of the target tissue, thus compromising the repair. The entrapment of non-target tissue when knotting or closing a loop of suture may be referred to as tissue bridging or suture bridging, and is illustrated in more detail below. Described herein are devices and methods for suturing tissue that prevent the entrapment of non-target tissue when advancing a loop of suture around a target tissue. These methods and devices are particularly (but not exclusively) relevant to arthroscopic procedures, and particularly the arthroscopic repair of the meniscus of the knee. the shoulder rotator cuff, and the hip (e.g., labrium).

For example, described herein are methods of preventing the entrapment of non-target tissue when using a suture passer to pass multiple lengths of suture through a target tissue. This may also be referred to as a method of preventing the formation of tissue bridging or suture bridging, as they prevent the formation of tissue bridges of non-target tissue when arthroscopically passing a loop of suture around a target tissue. Such methods may include: passing a first length of suture through the target tissue so that a first limb of the first length of suture extends from the target tissue; connecting the first limb of the first length of suture through a threading aperture at the distal end region of the suture passer; sliding the threading aperture of the suture passer along the first limb of the first length of suture to guide the suture passer to the target tissue; and passing a second length of suture through the target tissue using the suture passer.

In general, a suture may be passed through a tissue (e.g., target tissue) multiple times. A suture may be referred to as including multiple lengths of suture. Thus, when referring to multiple lengths of suture, this may include multiple lengths of the same suture or multiple lengths of different sutures. For example, a first length of a suture (near the distal end of the suture) may be passed through a target tissue. After passing the suture through the target tissue, the portions of the suture on either side of the target tissue may be referred to as the limbs of the suture. For example, the distal end of a first length of suture passed through a target tissue may be referred to as the limb (e.g., the first limb or the distal limb) of the first length of suture. A region of the suture that is proximal to the first length of suture may form a second length of suture. This second length of suture may also be passed through the tissue (as described in greater detail below) and the proximal region of the second suture length may also be referred to as a limb (a proximal limb or a second limb) of the second length of suture. Additional lengths of suture may be made up of other regions of the elongate length of suture and may also be passed through the tissue. The first and second lengths of suture (or additional lengths of suture) may be formed from different regions of the same elongate suture; alternatively one or more lengths of suture may be formed from different (non-continuous) sutures.

Any appropriate suture material may be used. For example, surgical-grade sutures such as catgut (plain, chromic), silk, polyglycolic acid, polylactic acid, polydioxanone, nylon, polypropylene, ultra high molecular weight polyethylene (UHMWPE), etc.

The general method of preventing tissue bridging described above may be used as part of any appropriate surgical method where it is undesirable to use a cannula, including particularly arthroscopic methods, in any appropriate body region, including shoulder, knee, spine, etc.

For example, described herein are methods of preventing the entrapment of non-target tissue when using a suture passer to arthroscopically pass multiple lengths of suture through a meniscus of a patient knee. These methods may include: passing a first length of suture through the meniscus so that a first limb of the first length of suture extends from the meniscus; connecting the first limb of the first length of suture to a threading aperture at the distal end region of the suture passer; sliding the threading aperture of the suture passer along the first limb of the first length of suture toward the meniscus to position the suture passer near the meniscus; and passing a second length of suture through the meniscus.

Any of these methods may also include arthroscopically inserting the suture passer into the tissue (e.g., knee) and using the suture passer to pass the first length of suture through the target tissue. Any of these methods may also include withdrawing the suture passer from the tissue after passing the first length of suture. The first limb of the suture may be withdrawn with the suture passer. Any of these methods may also include loading the second length of suture into the suture passer when the suture passer is withdrawn from the patient, so that the suture passer may be used to pass the second length of suture through the tissue. For example, the second length of suture may be a proximal region of the suture forming the first length of suture, which may be connected to the suture passer so that it can be passed by a tissue penetrator on the suture passer. Any of these methods may also include loading the second length of suture into a second suture passer such that a different suture passer instrument is used to pass the subsequent length than that used to pass the first. This may be referred to as a suture passer exchange.

In general, the methods described herein use a length (e.g., leg) of suture that has already passed through or around a portion of the target tissue to guide or steer the suture passer in passing a second (or third, fourth, fifth, etc.) length of suture through or around the same target tissue to prevent tissue bridging. Thus any of the methods described herein may use a suture passer that has been adapted to slide along the first length of suture so that it can be guided back to the target tissue. Adaptations that allow the suture passer to slide along the first length of suture from outside of the body to the target tissue region, while preparing to pass the second length of suture through or around the target tissue region may include a so-called threading aperture into which the first (pre-passed) length of suture may be threaded. The first length/leg of suture may then be slid within the threading aperture so that the suture passer can be directed along the same pathway though the body to the target tissue that the first length/leg of suture took when exiting the body from the target tissue.

In some variations, the methods described herein may be used to pass a loop of suture completely around the meniscus from the inferior side of the meniscus, through the meniscus to the superior sides of the meniscus, and back through the meniscus to the inferior side. The suture may be knotted or otherwise secured to close the loop; thus it would be desirable to prevent entrapment of non-target (e.g., non-meniscus in this example) tissue. Thus, passing the first length of suture through the meniscus may include passing the first length of suture between the inferior and superior surfaces of the meniscus. In general, passing the first length of suture through the meniscus may include extending the first limb of the first length of suture out of the patient's body.

The first limb of the first length of suture may be connected to the threading aperture at the distal end region of the suture passer by, e.g., threading the first limb of the first length of suture through the threading aperture.

A threading aperture may be any appropriate opening and/or channel into which the first length of suture may be slid to guide the suture passer to the target tissue. The aperture may be referred to as an opening, a gap, a cleft, a hole, an eyelet, a hook, a channel, or the like. The threading aperture may be any appropriate size, though it is typically relatively small, having an outer diameter that is sufficiently low-profile so that it does not substantially interferer with the overall low-profile of the tissue penetrator jaw(s) and an inner diameter that is sufficiently large to permit relatively easy loading of the first length of suture after it has already been passed through the tissue. The threading aperture may project (e.g., perpendicular to) the tip and/or side of one of the jaws of the suture passer, or it may be formed through a jaw of the suture passer. For example, in some variations connecting the first limb of the first length of suture to the threading aperture comprises passing the first limb of the first length of suture through one or more of: an eyelet, a hook, or a channel. The eyelet, hook or channel may extend distally from the distal end region of a jaw of the suture passer. The threading aperture may be configured and/or adapted to allow and/or enhance sliding over the first length of suture. For example, the opening of the threading aperture may be oriented to allow the suture passer to be readily slid over the length of suture as it is moved towards the target tissue without snagging, tearing, or putting undue force on the length of suture, which may otherwise damage the suture and/or the tissue into which the first length of suture has been passed. For example, the opening or channel through the threading aperture may face distally when the suture passer is moved towards the target tissue. The threading aperture may also be coated or formed of a low-friction material or layer to enhance sliding of the length of suture through the aperture. The aperture of the threading aperture may be completely enclosed (e.g., as in an eyelet) or partially open (as in a hook). If the threading aperture is partially open, the threading aperture may be oriented so that any lateral opening e.g., the gap between the shank and the tip of the hook) is oriented so that the length of suture does not inadvertently fall out of the threading aperture during use.

In use, the first length of the suture (leg) that is threaded into the threading aperture may be held taught when placing the suture passer. For example, when sliding the threading aperture of the suture passer along the first limb of the first length of suture, the first length of the suture may be held taut while sliding.

As mentioned, these methods and devices may be particularly well suited for arthroscopically suturing a meniscus. When passing the first length of suture, a suture passer may be used to arthroscopically pass a first length of suture between the inferior and suture surface of the meniscus, on one side of a tear (radial or lateral) in the meniscus. This may be performed as previously described (see, e.g., U.S. patent application Ser. No. 13/462,773, filed May 2, 2012, published as US-2012-0283754) by first positioning a bending first jaw on the superior side, then axially sliding/extending a second jaw under the inferior surface of the meniscus so that the first and second jaws form an distal-facing opening around the torn meniscus; a tissue penetrator may then pass the distal end of a suture between the inferior and superior sides of the meniscus. After withdrawing the suture passer, the distal end of the first length of suture (the distal leg) extends out of the knee region, and possibly out of the patient. The proximal end of the suture may remain in the suture passer. The suture passer can then be removed from the meniscus (e.g., by reversing the steps used to position it) and reloaded, or it can remain loaded with the rest of the suture proximal to the distal end. The suture passer may be completely removed from the knee. The distal end of the first length of suture (the distal leg) can then be threaded through the treading aperture at the distal end of the device, and the first length of suture can be held taut from outside of the knee while sliding the suture passer, which has also been loaded or prepared to pass a second length of the suture, back into the meniscus on another side of the tear. The first and second jaws can again be positioned on either side of the meniscus and the tissue penetrator extended between them to pass the suture and complete the loop around and through the meniscus so that both ends of the suture are on the same side of the meniscus. A pre-tied knot can then be slid down the suture and the loop of suture closed (knotted). Thus, in this method the second length of suture may be passed through the meniscus by first using the first length of suture to guide the suture passer to the meniscus, so that when knotting the loop of suture, non-target tissue does not get held up by the knot, preventing tissue bridging.

Another example of the method of preventing the entrapment of non-target tissue when using a suture passer to pass multiple lengths of suture through a meniscus of a patient knee comprises: arthroscopically passing a first length of a suture through the meniscus between an inferior surface of the meniscus and a superior surface of the meniscus using a suture passer so that a first limb of the first length of suture extends from the meniscus and out of the patient's body; connecting the first limb of the first length of suture to a threading aperture at the distal end region of the suture passer; holding the first limb of the first length of suture taut; sliding the threading aperture of the suture passer along the first limb of the first length of suture toward the meniscus to position the suture passer near the meniscus; passing a second length of the suture through the meniscus between the inferior surface of the meniscus and the superior surface of the meniscus; withdrawing the suture passer from the meniscus; and sliding a pre-tied knot to knot the first length of suture and the second length of suture through the meniscus.

Suture passer devices are also described herein. In general, suture passer devices configured to prevent entrapment of non-target tissue when forming a loop of suture through or around target tissue include a threading aperture at a distal end region of the device to allow the suture passer to pass a second length of suture by sliding along a first length of suture passed through a target tissue from outside of the patient to the target tissue. In some variations these suture passers are the meniscus suture passers previously described, but including a threading aperture. For example, described herein are suture passer devices configured to prevent the entrapment of non-target tissue when inserting the device into the tissue multiple times to form a loop of suture around a target tissue. These devices may include: a first jaw member extending distally from an elongate body; a second jaw member extending distally from the elongate body, wherein the first jaw member and the second jaw member are configured to form a distal-facing mouth; a threading aperture at the distal end region of the first jaw member and configured to slide along a first length of suture to guide the suture passer to the target tissue; and a tissue penetrator extendable between the distal-facing mouth formed by the first jaw member and the second jaw member to pass a second length of suture between the first jaw member and the second jaw member.

As mentioned above, any appropriate threading aperture may be used, including an eyelet, a hook, a channel, or the like. The first jaw member may be pivotally coupled to the distal end region of the elongate body, and configured to pivot relative to the elongate body. The second jaw member may be slideably extendable distally from the elongate body. In some variations, the second jaw member may be slideably extendable distally from the elongate body to one or more set stop positions. The set stop positions may comprise set positions from which the tissue penetrator may extend across the distal-facing mouth to pass a length of suture between the first jaw member and the second jaw member.

For example, also described herein are suture passer devices configured to prevent the entrapment of non-target tissue when inserting the device into the tissue multiple times to form a loop of suture around a target tissue, the device comprising: a first jaw pivotally coupled to a distal end region of an elongate body, wherein the first jaw is configured to pivot relative to the elongate body; a threading aperture at a distal end region of the first jaw and configured to slide along a first length of suture to guide the suture passer to the target tissue; a second jaw slideably extendable distally from the elongate body, wherein the first jaw and the second jaw are configured to form a distal-facing mouth; and a tissue penetrator configured to extend across the distal-facing mouth to pass a second length of suture between the first and second jaw members.

BRIEF DESCRIPTION OF THE DRAWINGS

FIGS. 3A-3L illustrate a method of arthroscopically repairing a torn meniscus as described herein wherein the method is adapted to prevent the entrapment of non-target tissue when using a suture passer to arthroscopically pass multiple lengths of suture through the meniscus. The numbering of FIGS. 3A-3K corresponds approximately to that of FIGS. 2A-2K; FIGS. 3H1 and 3H2 indicate the steps replacing FIG. 2H. FIG. 3L illustrates knotting the loop of suture passed without forming the tissue bridge of entrapped tissue.

DETAILED DESCRIPTION

Described herein are devices and methods for preventing entrapment of non-target tissue (e.g., tissue bridging) when using a suture passer to form a loop (or loops) of suture through and/or around a target tissue. In particular, described herein are devices and systems for passing a loop of suture through and/or around a torn meniscus of the knee without forming a tissue bridge.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Figure 1B:
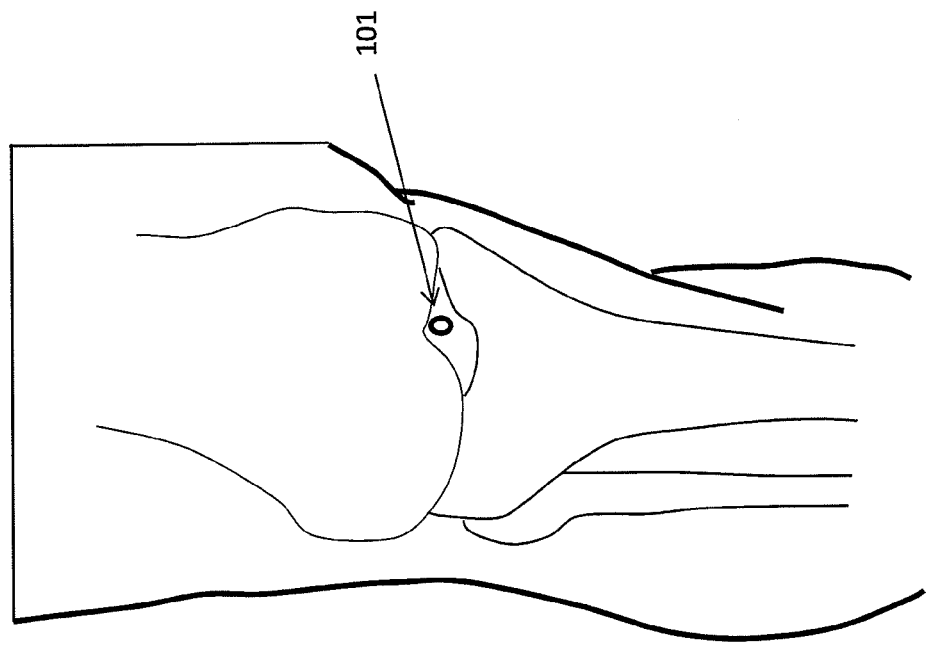
FIGS. 1A to 1C illustrate an arthroscopic approach to surgery on the meniscus of the knee.
Figure 1A:
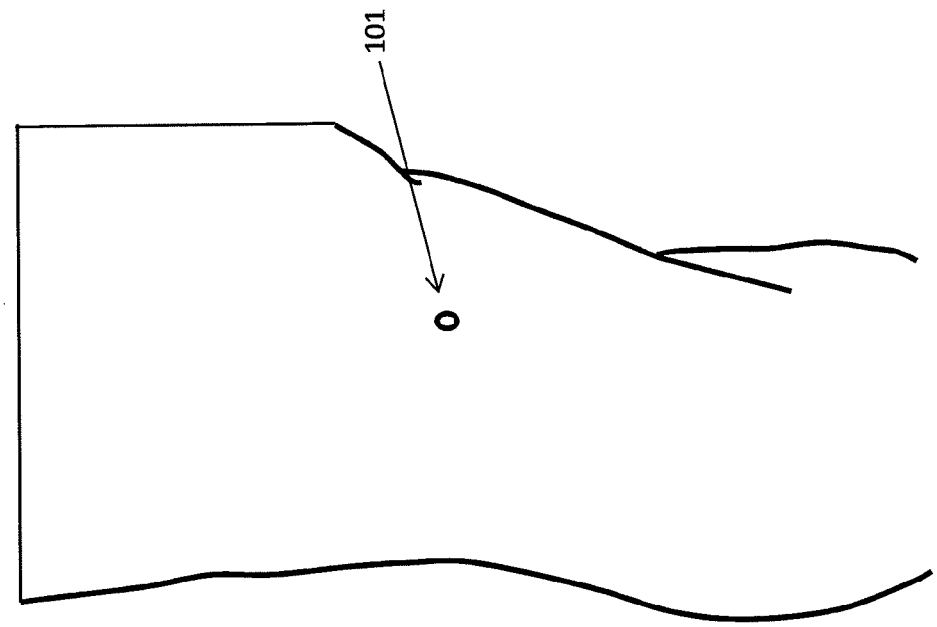
Figure 1C:
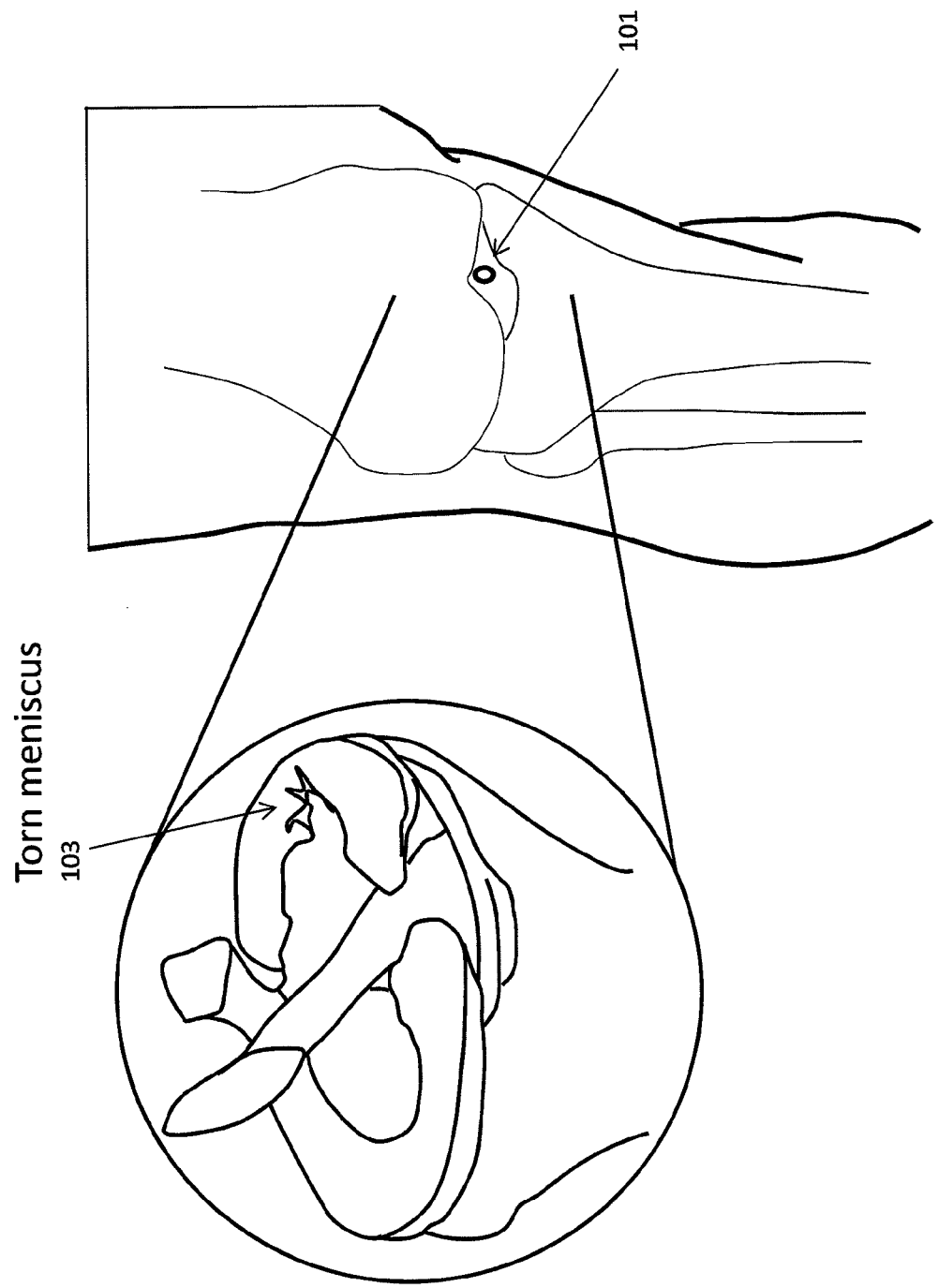
Figure 1D:
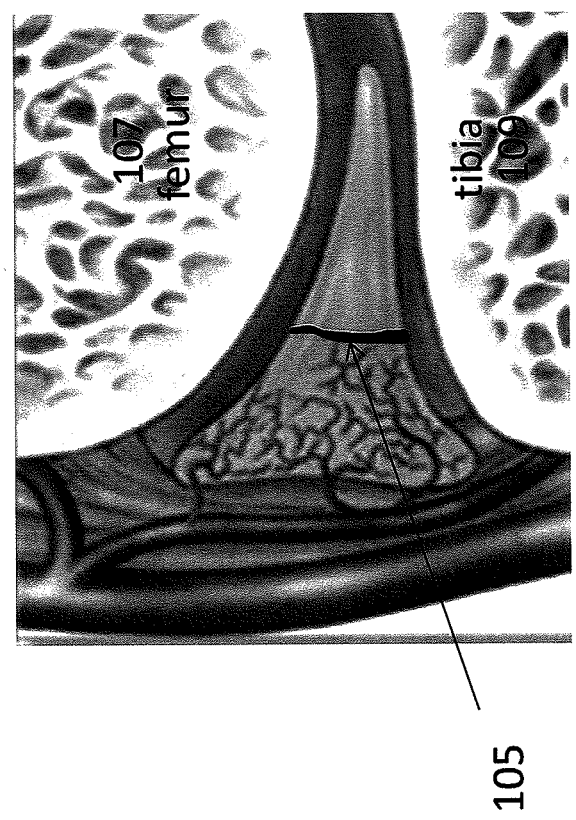
FIG. 1D illustrates a torn meniscus within the knee.

As discussed above, tissue bridging involves the inadvertent capture of non-target tissue by a loop of suture when passing the suture around and/or through a target tissue. This may prevent the target tissue from being secured (e.g., knotted) and is undesirable. Tissue bridging is particularly problematic when suturing arthroscopically, and particularly in difficult-to-access areas such as the meniscus of the knee. FIGS. 1A-1D illustrate one example of arthroscopic access and repair of a knee. For example, in FIG. 1A, one more small access ports 101 may be formed into the knee in order to provide access using minimally invasive tools such as a suture passer as described below. FIG. 1B illustrates the knee of in which the tissue surrounding the bones forming the knee joint have been made partially transparent. The two semi-circular menisci are located between the femur and tibia in the knee joint. In FIG. 1C, the torn meniscus 103 has been made visible in the expanded region by removing the femur head from the expanded version. The superior surface of the meniscus, which is normally covered by the femur head, is visible, and the torn region is also apparent. FIG. 1D illustrates a sectional view through the intact knee region showing the relationship between the torn meniscus 105, and it location between the femur head 107 and the tibial plateau 109. The apex of the meniscus is shown on the right.

Thus, the meniscus is very difficult to access to repair in the intact knee because of the tight positioning between the femur and the tibia. Recently, suture passers that may be reliably used within the spatial confines of the relatively intact knee have been described, as mentioned above, which may be used to repair the meniscus in the intact or semi-intact knee, and may form a loop of suture through the meniscus from the superior-to-inferior surfaces and back again. However, these suture passers, as well as other prior art suture passers, may still result in tissue bridging, especially when removing the suture passer from the knee between passing lengths of suture. This problem is illustrated in FIGS. 2A-2F.

Figure 2A:
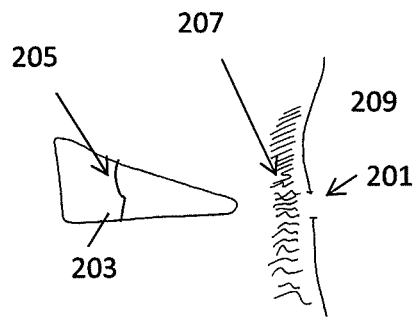
FIGS. 2A to 2K illustrate a method of arthroscopically repairing a torn meniscus in the knee using a suture passer to form a loop of suture around a torn meniscus, resulting in tissue bridging (FIG. 2K).

For example, in FIG. 2A, a meniscus 203 is shown including a tear 205 (for convenience, the tear is not shown in the remaining figures, though is still present), within the patient's knee (as illustrated above in FIGS. 1A-D). An opening 201 has been made into the knee so that the meniscus can be accessed arthroscopically. Other access points may also be provided (e.g., for imaging, probes, etc.). Non-target tissue 207 may intervene between the meniscus 203 and the opening 201, even after making the opening. In some variations an access tube or channel may be used (not shown), which may help prevent the intervening non-target tissue 207 from blocking or even partially occluding access to the meniscus from outside of the knee 209.

Figure 2B:
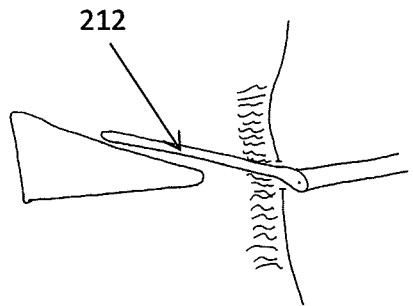
Figure 2C:
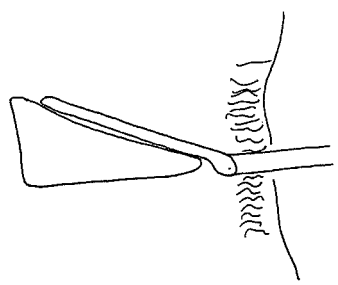
Figure 2D:
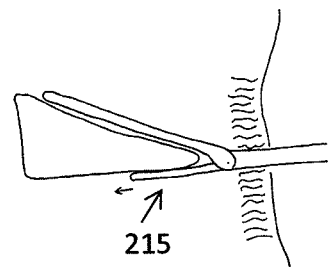
Figure 2E:
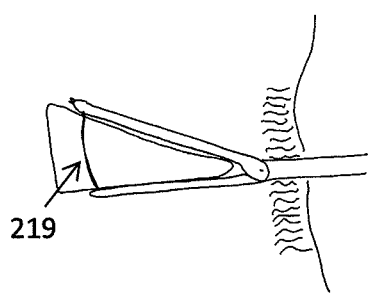

In FIG. 2B the distal tip of a suture passer 212 having a first jaw member that extends from the distal end of the body of the suture passer is shown accessing the superior surface of the meniscus between the head of the femur (not shown) and the superior surface of the meniscus. In some variations this upper jaw member may be bendable relative to the elongate body of the suture passer, which may allow the angle of the upper jaw member to be adjusted when positioning it between the superior surface of the meniscus and the femoral head, as shown in FIGS. 2B and 2C. In FIG. 2B, the upper jaw is adjacent to the superior meniscus and between the superior surface and the femoral head. Once the upper jaw is positioned, the lower jaw 215 of the suture passer is extended from within the elongate body of the suture passer, as shown in FIG. 2D (arrow), to form a distal-facing jaw around the apical region of the meniscus. Thereafter, the suture may be passed between the two jaw members. In this example, the suture is passed from the inferior side (e.g., the lower jaw member) to the superior side (e.g., upper jaw member) using a tissue penetrator 219 that extends from the lower jaw member and through the meniscus tissue to push the distal end region (distal length of suture) from the lower jaw to the upper jaw member, as shown in FIG. 2E. The distal end of the suture is retaining by the upper (first) jaw member and the tissue penetrator is retracted back to the lower (second) jaw member. However, in some variations the length of suture may be passed from the upper jaw member to the lower jaw member. For example, the tissue penetrator may be configured to pull the suture passer through the tissue from the upper jaw to the lower jaw (or vice versa). Alternatively, the tissue penetrator may be configured to extend from the upper jaw to the lower jaw, and either push or pull the length of suture.

Figure 2F:
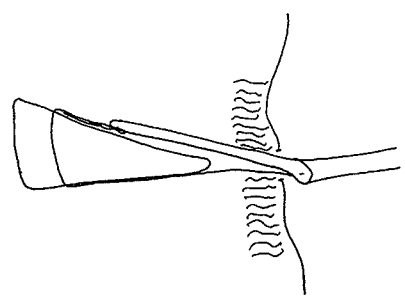
Figure 2G:
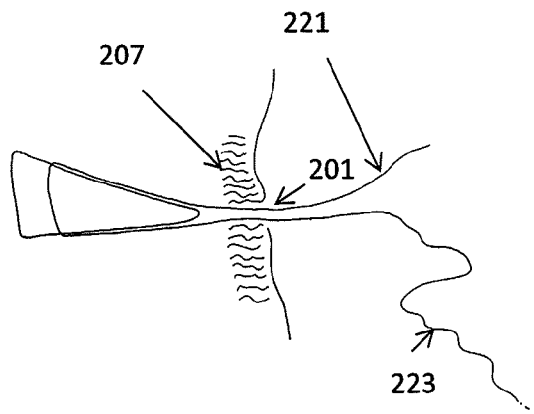

Once the first length of suture has been passed, as shown in FIG. 2F, the suture passer may be retracted by reversing the steps for inserting it over the meniscus shown above in FIGS. 2A-2D), e.g., first withdrawing the lower jaw member (not shown) and the removing the upper jaw member along the superior surface of the meniscus. This leaves a length of the suture (from the distal end of the suture 221) through the meniscus in the path taken by the tissue penetrator, with the end of the suture extending out of the knee through the opening 201 formed to provide access, as shown in FIG. 2G. The more proximal length of the suture 223 may also exit the knee with the suture passer. The suture is drawn through the passed stitch as the upper raw is withdrawn (not shown). The suture passer in this example, is then re-loaded outside of the knee so that it may pass another (e.g., second) length of suture from the region of the suture that is proximal to the distal end length of suture.

Figure 2H:
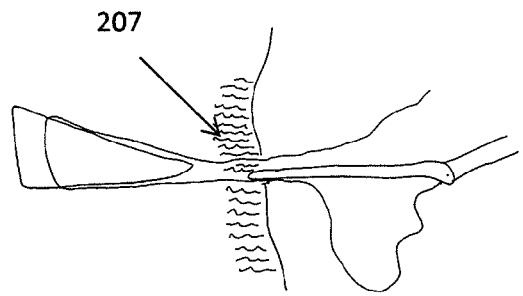
Figure 2I:
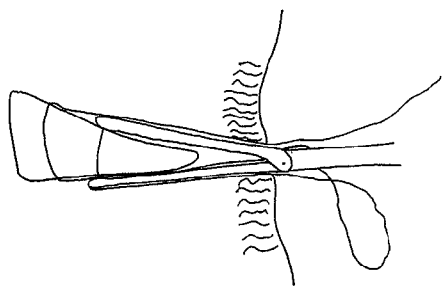
Figure 2J:
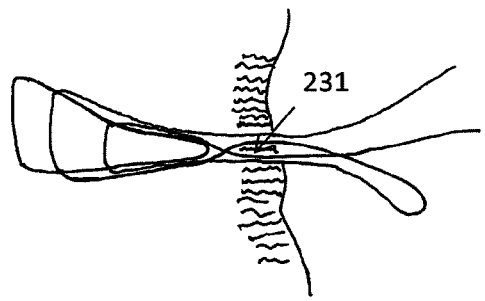
Figure 2K:
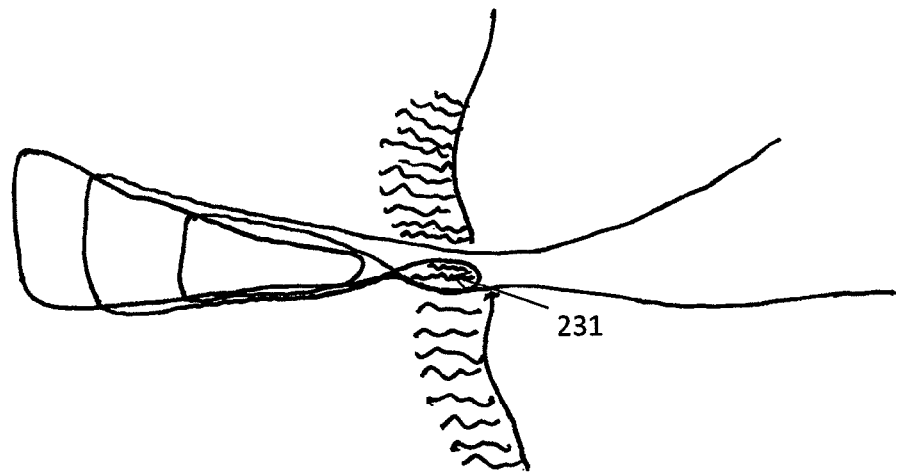

As shown in FIG. 2H, the distal end of the suture passer (e.g., the first jaw member) can then be re-inserted into the same opening 201 that the suture passer used to access to pass the first suture. Thus, the distal end region of the suture passer must again pass through the intervening non-target tissues 207. The distal end of the device may also pass by the first length of suture 221. The suture passer may again be positioned between the superior meniscal surface and the femoral head, as shown in FIG. 2I, and the lower jaw extended to form a distal-facing mouth within which the apex of the meniscus fits. The location of the suture passer on the meniscus is typically different from the initial position (e.g., FIG. 2E), so that a complete loop of suture surrounding at least a portion of the tear may be sutured. This may be accomplished by again passing the tissue penetrator through the tissue (as shown in FIG. 2I) to pass the next length of suture through the meniscal tissue on the other side of the tear from the first pass. In this case, the suture is shown passing from the inferior side back to the superior side, and the suture passer is again retracted from the tissue, pulling the legs of the length of suture to tighten the loop as the suture passer is withdrawn, as shown in FIG. 2J. Unfortunately, as illustrated in this example, a tissue bridge 231 has been formed by the length of suture, capturing non-target tissue 207 within the tightening loop of suture as it is retracted. Thus, as shown in FIG. 2K, the non-target tissue forms a part of the loop through the meniscus, and prevents the loop from being tightened around the meniscal tear. Another (alternatively or additionally) tissue bridge may be formed at the superior side if the path exiting the meniscus taken by the distal leg of the first length of suture 221 through the tissue and out of the subject is slightly different than the path taken by the proximal end of the second length of suture taken to exit the tissue. Thus, when pushing or forming a knot to tie off the proximal and distal ends of the suture and close the loop around/through the target tissue, captured non-target tissue 207 will prevent the loop from being tightened or closed completely.

Described herein are suture passer devices that may address this problem, and be used in methods for forming a loop of suture around/through the target tissue without substantially capturing non-target tissues. One variations of a method of suturing tissue to prevent tissue bridging is illustrated in FIGS. 3A-3L. In this example, the numbering of the figures and figure elements has been correlated to FIGS. 2A-2K, so that the figures and elements can be compared side-by-side to illustrate the methods described.

Figure 3A:
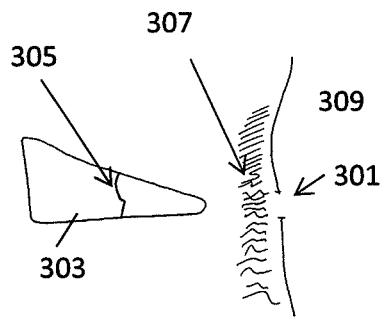
Figure 3B:
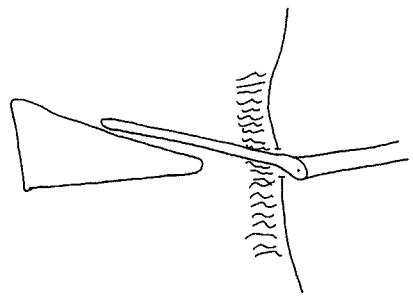
Figure 3C:
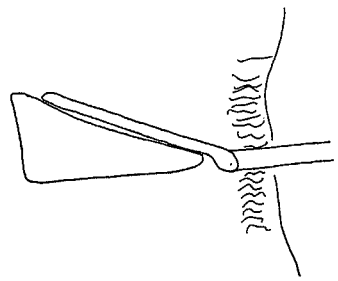
Figure 3D:
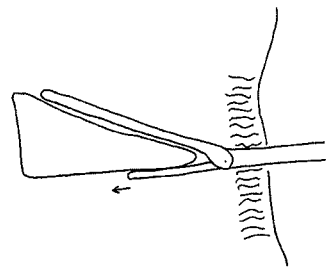
Figure 3E:
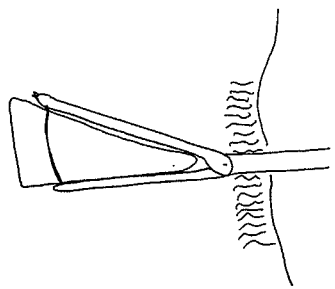
Figure 3F:
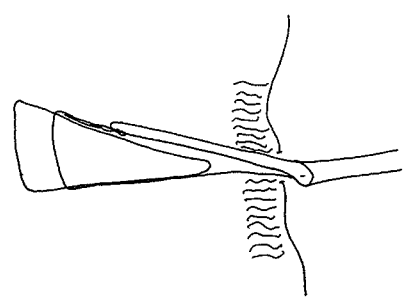
Figure 3G:
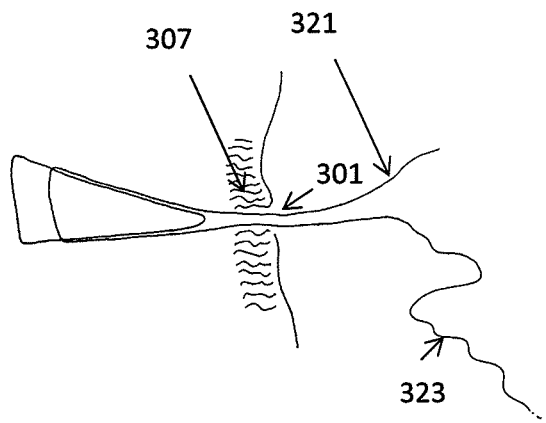
Figure 3I:
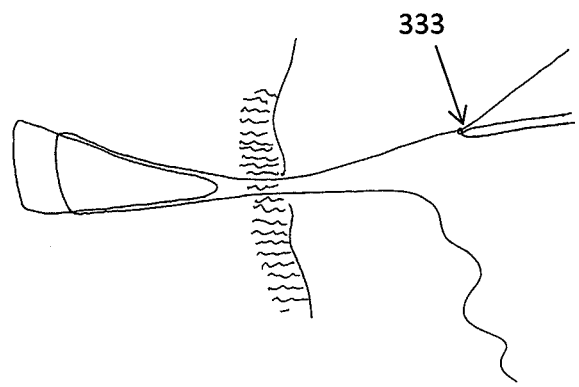
Figure 3I:
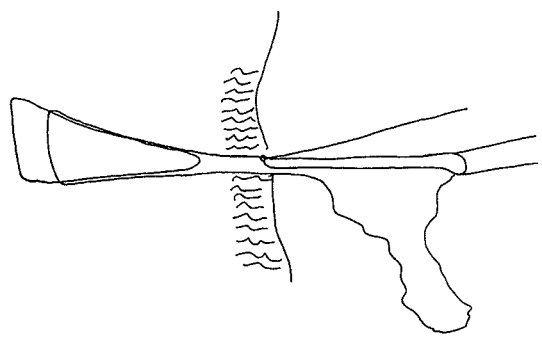
Figure 3I:
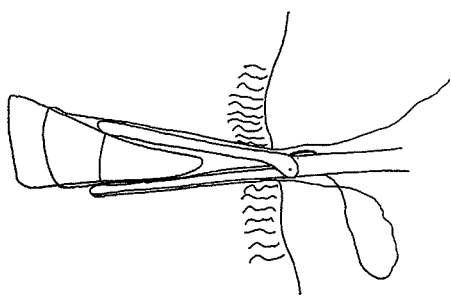
Figure 3J:
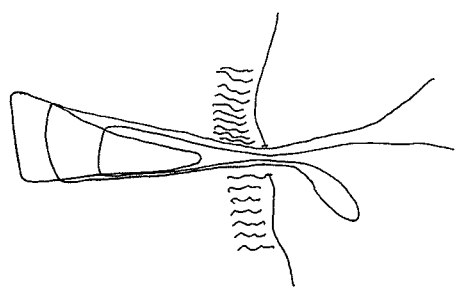
Figure 3K:
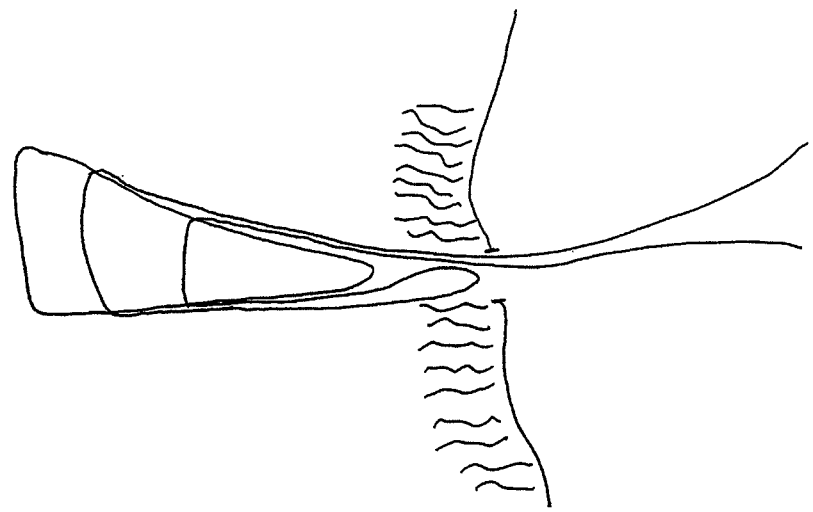
Figure 3L:
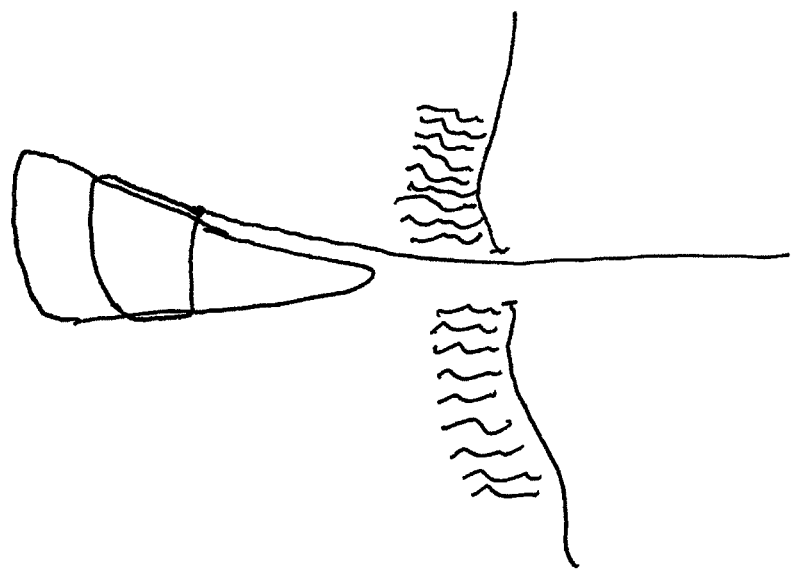

As just discussed, and as illustrated in FIGS. 2A-2G, the suture passer may be used to minimally invasively repair a torn 305 meniscus 303 by endoscopically entering the patient's knee with a suture passer from a relatively small opening 301 from outside of the patient 309. The suture passer may be inserted so that the first jaw member is positioned between the superior surface of the meniscus and the femoral head (as shown in FIG. 3C), and the lower jaw member is then extended to pass the first length of suture across one side of a tear in the meniscus, as shown above for FIGS. 2A-2F, corresponding to FIGS. 3A-3F. Once the suture passer has been withdrawn, as shown in FIG. 3G (corresponding to FIG. 2G), the distal end of the first leg of suture 321 and the proximal length of suture 323 (proximal to the distal length that was passed through the tissue) both extend from the opening in the knee. The proximal length of suture is loaded (or re-loaded) on to the suture passer (e.g., in the lower jaw member (not shown). In this example, as shown in FIG. 3H1, the suture passer includes a threading aperture 333 into which the distal end of the first leg of the first length of suture 321 is loaded. This threading aperture is located at the distal tip of the first jaw member of the suture passer. In use, the distal end of the first leg 321 of suture is held taut while the suture passer (the threading aperture) is passed over the suture and used to guide the tissue passer back to the meniscus along approximately the same path as taken by the suture passer when placing the first length of suture through the meniscus, as shown in FIG. 3H2. When the suture passer is reasonably near the meniscus, it may be repositioned relative to the meniscus, as shown in FIG. 3I, so that the second length of suture may be passed through the meniscus on another side of a meniscal tear. Thereafter, the steps may be reversed, and the suture passer withdrawn from the knee, leaving the proximal and distal lengths of suture (as well as a portion of the loop between them) outside of the knee, which can then be drawn taut and knotted, as shown in FIGS. 3K and 3L. In this example, because the path into the knee was guided by the threading aperture, non-target tissue was not entrapped between different lengths of suture.

Suture-Passers Including a Threading Aperture

Any appropriate suture passer may be adapted to prevent tissue bridging as described herein. In particular, a suture passer may include a threading aperture at or near a distal end of the suture passer so that a leg of suture that has already been passed on and/or around a target tissue may be used to guide the suture passer device back near the tissue while avoiding the inadvertent capture of non-target tissue that may arise when the path through non-target tissue is not the same for different lengths of a suture forming a loop around/through the target tissue.

Figure 4A:
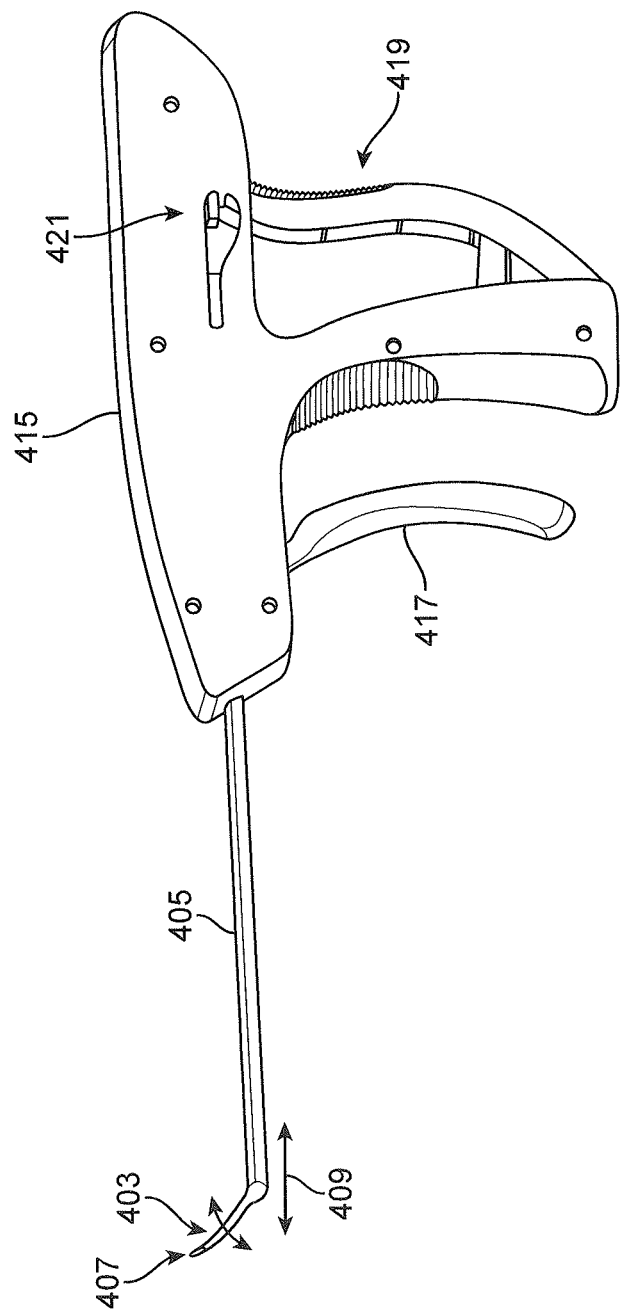
FIGS. 4A and 4B illustrate one variation of a suture passer including a threading aperture that may be used to prevent entrapment of non-target tissue when using the suture passer to arthroscopically pass multiple lengths of suture.
Figure 4B:
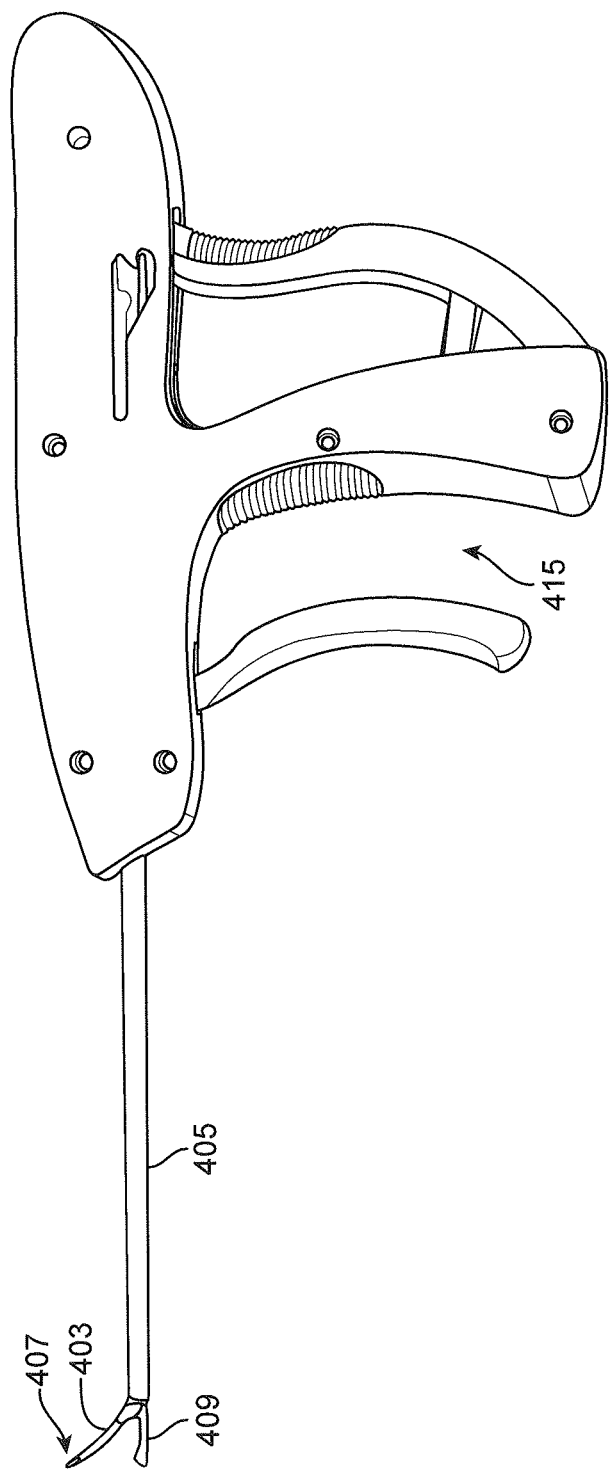

Suture passers having independently controllable jaw members (e.g., an axially retractable jaw member and/or a hinged or bendable jaw member), such as may be used for meniscus repair are one example, as illustrated in FIGS. 4A and 4B. In this example, the suture passer includes a distal end having a hinged upper jaw 403 that can change its angle relative to the elongate body member 405. A threaded aperture 407, which is described in greater detail below, is shown near the distal end of the hinged upper jaw member 403. A lower jaw member (not visible in FIG. 4A, but extended in FIG. 4B) 409 may move axially relative to the elongate body 405 to form a distal facing opening with the hinged upper jaw member 403. The suture passer in this example also includes a handle 415 with a grip and a number of actuating controls, including an upper jaw control 417 and a lower jaw control 419, as well as a lower jaw retractor 421.

Figure 5C:
FIGS. 5A-C illustrate variations of threading apertures that may be included with a suture passer as described herein.
Figure 5B:
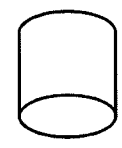
Figure 5A:
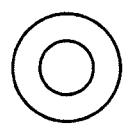

As mentioned above, a threaded aperture may be any shay or configuration, particularly those that allow relatively easy sliding and/or loading onto the suture leg extending from the body after having been passed through the tissue. The threaded apertures therefore typically allow sliding of the suture within the opening without snagging, and may hold the suture securely, or be releasable from the length of suture. FIGS. 5A to 5C illustrate three examples of threading apertures that may be used. These threading apertures may be sized and coupled to the suture passer so as to prevent interference with the relatively low-profile configuration of the distal end of the suture passer.

For example, a threading aperture may include an eyelet or ring-shape as illustrated in FIG. 5A. The eyelet may have an opening thorough a relatively narrow toroidal body. In some variations the inner surface(s) of the threading aperture is coated or formed of a low-friction material that enhances sliding of the threaded aperture along the suture length (leg). FIG. 5B shows another variation of a threading aperture having a cylindrical shape with a length as well as an opening. In FIG. 5B the length may be varied as desired (e.g., <1 mm, <2 mm, <3 mm, <5 mm, <1 cm, <2 cm, <3 cm, <5 cm, <10 cm, or longer). In some variations, the length may be a channel or passage into which the suture fits. In some variations, the channel may include an opening along the length, to allow relatively easy loading, similar to the hook variation shown in FIG. 5C.

In FIG. 5C, the threading aperture is a hook having an opening into which the suture length may be passed. Alternatively, the threading apertures may be spiral openings (e.g., for holding the suture within the spiral channel, but preventing it from accidentally exiting). Other configurations are possible.

Figure 6A:
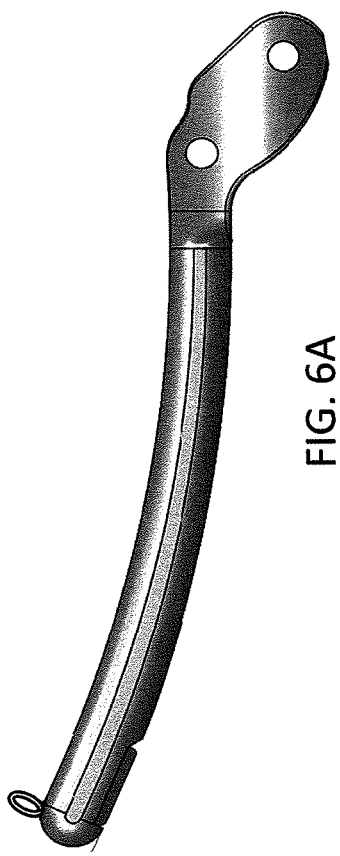
FIGS. 6A and 6B illustrate variations of the distal end (e.g., jaw member) of a suture passer including one variation of a threading aperture.
Figure 6B:
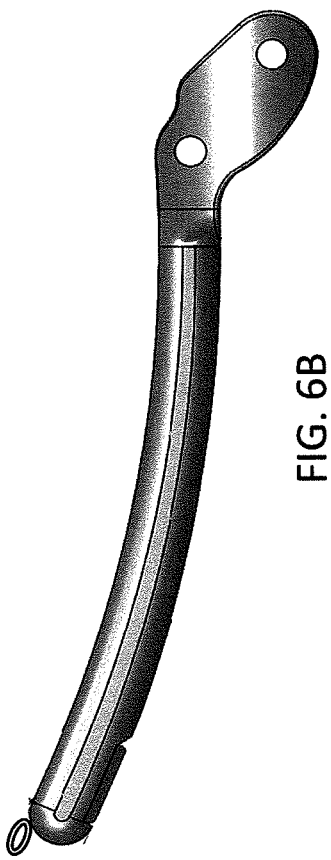

The threading aperture may be positioned at or near the distal end of the suture passer, including at or near the distal end or distal end region of one of the jaw members of a suture passer, as shown in FIGS. 6A and 6B in alternative configurations. In FIG. 6A, the threading aperture is configured as an eyelet shape that extends transversely from the distal end region of the jaw member. Alternatively, in FIG. 6B, the eyelet threading aperture is shown extending in the line of the jaw member, from the distal tip of the jaw member. In some variations the threading aperture is formed through the jaw member rather than extending from it.

Figure 7A:
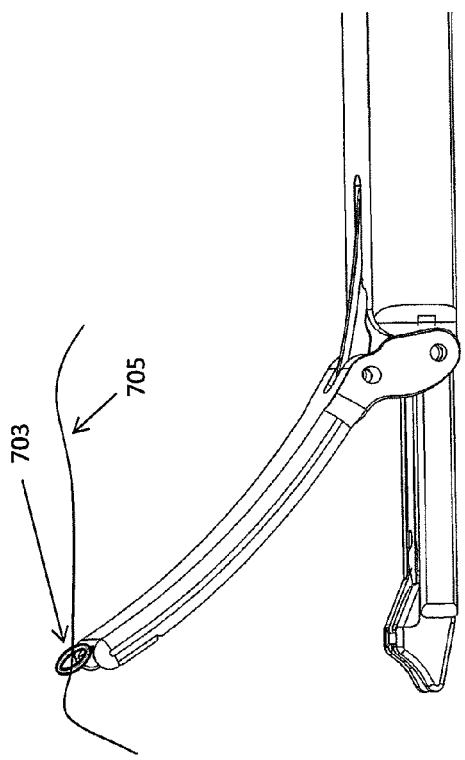
FIGS. 7A and 7B illustrate operation of one variation of a suture passer including a threading aperture, similar to the threading aperture configuration shown in FIG. 6B.
Figure 7B:
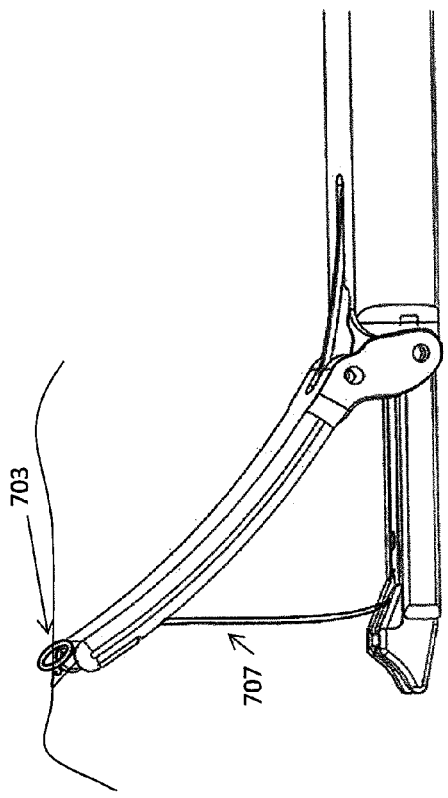

FIGS. 7A and 7B illustrate operation of one variation of a threading aperture 703 such as the eyelet variation shown in FIGS. 5A and 6B. In this example, the tissue penetrator 707 may pass through tissue within the distal-facing opening of the suture passer (when both jaws are extended) and the eyelet 703 does not interfere with the tissue penetrator 707, nor does a suture 705 within the eyelet interfere with activity of the tissue penetrator.

Figures 8A, 8B:
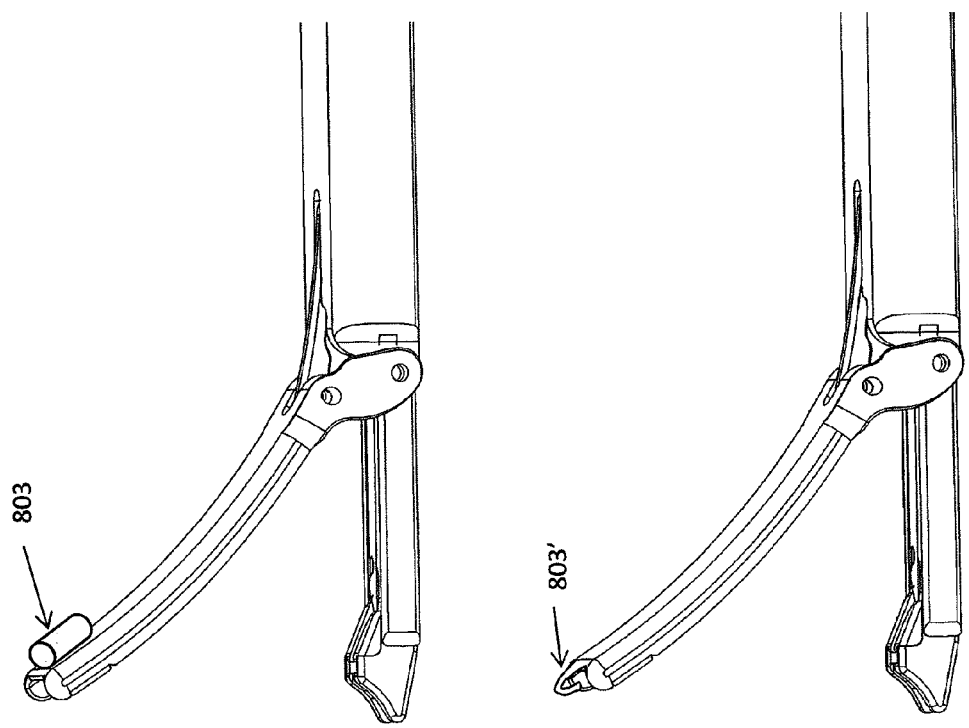
FIG. 8A-8D illustrate variations of the distal end of suture passers including different variations of threading apertures.
Figure 8C:
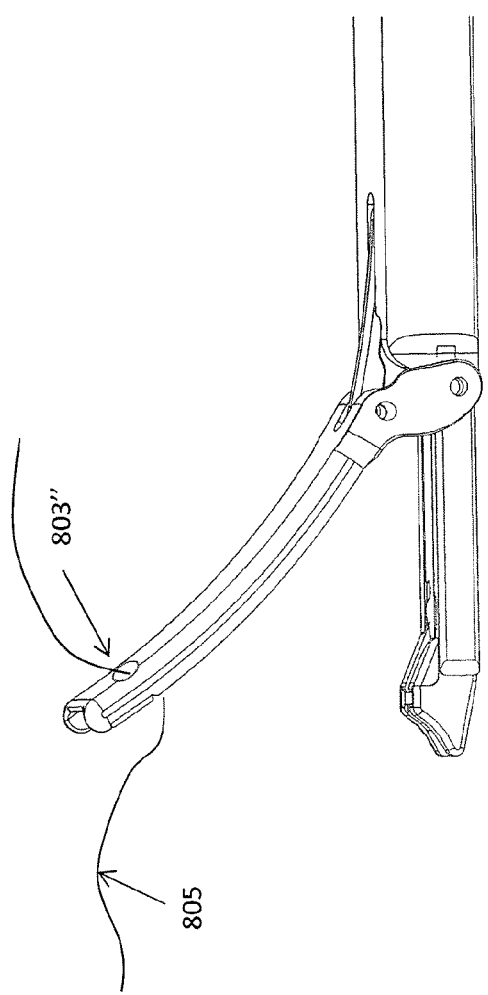
Figure 8D:
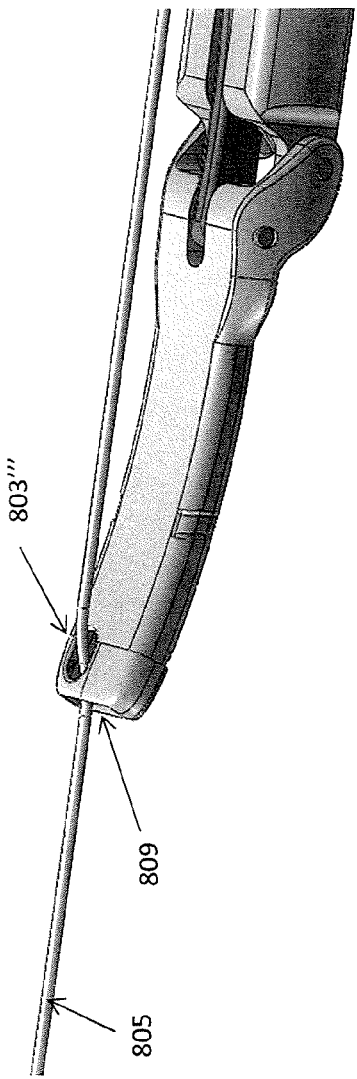

FIGS. 8A to 8D illustrate other variations of threading aperture at the distal end regions of a suture passer that may be used as described above. For example, in FIG. 8A, the threading aperture 803 in this example is a hollow cylinder into which the suture may be passed and used to guide placement of the suture passer. The cylinder is positioned oriented with the long axis of the upper jaw member in this example. In FIG. 8B, the threading aperture is shown as a hook member 803' that is extending distally from the distal end of the upper jaw member. FIG. 8C illustrates an alternative variation in which the threading aperture is an opening through the suture passer. A suture 805 may be passed completely through the distal end region of the device, as illustrated. The location of this opening through the jaw member may be different. For example, the opening (threading aperture 803") may be oriented along the long axis (e.g., the exit may pass from the distal opening of the suture passer, or to one size of the midline of the suture passer (rather than directly through the midline, as shown). FIG. 8D is similar to the variation shown in FIG. 8C, however, the threading aperture 803'" forms a passage through the jaw of the suture passer that exits from the distal-facing opening 809 at the distal end of the bendable jaw member; the tissue penetrator may also exit from this distal opening 809 when it is extended across the device, to deflect the tissue penetrator distally.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of preventing the entrapment of non-target tissue when passing multiple lengths of suture through a target tissue, the method comprising:
   passing a first length of suture through the target tissue so that a first limb of the first length of suture extends from the target tissue;
   connecting the first limb of the first length of suture through a threading aperture at the distal end region of a suture passer;
   sliding the threading aperture of the suture passer along the first limb of the first length of suture to guide the suture passer to the target tissue; and
   passing a second length of suture through the target tissue using the suture passer.

2. A method of preventing the entrapment of non-target tissue when arthroscopically passing multiple lengths of suture through a meniscus of a patient knee, the method comprising:
   passing a first length of suture through the meniscus so that a first limb of the first length of suture extends from the meniscus;
   connecting the first limb of the first length of suture to a threading aperture at the distal end region of a suture passer;
   sliding the threading aperture of the suture passer along the first limb of the first length of suture toward the meniscus to position the suture passer near the meniscus; and
   passing a second length of suture through the meniscus.

3. The method of claim 2, wherein passing the first length of suture through the meniscus comprises using the suture passer to pass the first length of suture through the meniscus.

4. The method of claim 2, wherein passing the first length of suture through the meniscus comprises using a second suture passer to pass the first length of suture through the meniscus.

5. The method of claim 2, wherein passing the first length of suture through the meniscus comprises passing the first length of suture between the inferior and superior surfaces of the meniscus.

6. The method of claim 2, wherein passing the first length of suture through the meniscus comprises extending the first limb of the first length of suture out of the patient's body.

7. The method of claim 2, wherein connecting the first limb of the first length of suture to the threading aperture at the distal end region of the suture passer comprises threading the first limb of the first length of suture through the threading aperture.

8. The method of claim 2, wherein connecting the first limb of the first length of suture to the threading aperture comprises passing the first limb of the first length of suture through one or more of: an eyelet, a hook, or a channel.

9. The method of claim 2, wherein sliding the threading aperture of the suture passer along the first limb of the first length of suture comprises holding the first length of the suture taut while sliding.

10. The method of claim 2, wherein passing the second length of suture through the meniscus comprises passing a second length of the same suture forming the first length of suture through the meniscus.

11. The method of claim 2, wherein passing the second length of suture through the meniscus comprises passing the second length of suture between the inferior and superior surfaces of the meniscus.

12. The method of claim 2, further comprising withdrawing the suture passer from the meniscus after passing the second length of suture.

13. The method of claim 2, further comprising sliding a pre-tied knot to knot the first length of suture and the second length of suture through the meniscus.

14. A method of preventing the entrapment of non-target tissue when using a suture passer to pass multiple lengths of suture through a meniscus of a patient knee, the method comprising:
   arthroscopically passing a first length of a suture through the meniscus between an inferior surface of the meniscus and a superior surface of the meniscus using a suture passer so that a first limb of the first length of suture extends from the meniscus and out of the patient's body;
   connecting the first limb of the first length of suture to a threading aperture at the distal end region of the suture passer;
   holding the first limb of the first length of suture taut;
   sliding the threading aperture of the suture passer along the first limb of the first length of suture toward the meniscus to position the suture passer near the meniscus;
   passing a second length of the suture through the meniscus between the inferior surface of the meniscus and the superior surface of the meniscus;
   withdrawing the suture passer from the meniscus; and
   sliding a pre-tied knot to knot the first length of suture and the second length of suture through the meniscus.

* * * * *